United States Patent
Ja et al.

(10) Patent No.: US 11,520,084 B2
(45) Date of Patent: *Dec. 6, 2022

(54) IRRADIATION SYSTEM FOR MULTIWELL INACTIVATION

(71) Applicant: Phoseon Technology, Inc., Hillsboro, OR (US)

(72) Inventors: Shiou-jyh Ja, Portland, OR (US); Scott Igl, Portland, OR (US)

(73) Assignee: Phoseon Technology, Inc., Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/182,730

(22) Filed: Feb. 23, 2021

(65) Prior Publication Data

US 2021/0173125 A1 Jun. 10, 2021

Related U.S. Application Data

(63) Continuation of application No. 16/421,263, filed on May 23, 2019, now Pat. No. 10,955,590.

(Continued)

(51) Int. Cl.
*G02B 3/00* (2006.01)
*A61L 2/00* (2006.01)

(52) U.S. Cl.
CPC .......... *G02B 3/0068* (2013.01); *A61L 2/0047* (2013.01)

(58) Field of Classification Search
CPC .. G01N 2800/56; G01N 29/04; G01N 29/075; G01N 29/221; G01N 30/0005; G01N 30/28; G01N 30/463; G01N 30/52; G01N 30/56; G01N 30/6065; G01N 30/7286; G01N 30/8658; G01N 30/90; G01N 30/92; G01N 31/22; G01N 31/221; G01N 33/15; G01N 33/1826; G01N 33/487; G01N 33/48792; G01N 33/4915;
(Continued)

(56) References Cited

U.S. PATENT DOCUMENTS 6,198,577 B1 3/2001 Kedar et al.
6,473,239 B2 10/2002 Völcker et al.
(Continued)

FOREIGN PATENT DOCUMENTS

JP H02302650 A * 12/1990
JP 2005530140 A * 10/2005
(Continued)

OTHER PUBLICATIONS

ISA Korean Intellectual Property Office, International Search Report and Written Opinion Issued in Application No. PCT/US2019/033846, dated Aug. 30, 2019, WIPO, 11 pages.

*Primary Examiner* — Michael P Stafira
(74) *Attorney, Agent, or Firm* — McCoy Russell LLP

(57) ABSTRACT

A system for irradiating a microplate may include a light engine with a plurality of light sources, such as light-emitting diodes, included in one or more linear arrays. The plurality of light sources are configured to emit germicidal irradiation, which is directed to the microplate by optical components, such as optical lenses positioned on top of each well of the microplate. The linear array is linearly movable so that as the linear array scans across the microplate, the optical components direct the germicidal irradiation to a plurality of surfaces of each well.

20 Claims, 9 Drawing Sheets

Related U.S. Application Data

(60) Provisional application No. 62/678,904, filed on May 31, 2018.

(58) Field of Classification Search
CPC ........... G01N 33/5035; G01N 33/5047; G01N 33/5067; G01N 33/5082; G01N 33/5088; G01N 33/5094; G01N 33/521; G01N 33/535; G01N 33/54313; G01N 33/54333; G01N 33/545; G01N 33/563; G01N 33/56966; G01N 33/56988; G01N 33/56994; G01N 33/57415; G01N 33/579; G01N 33/60; G01N 33/6845; G01N 33/6875; G01N 33/6881; G01N 33/6887; G01N 33/80; G01N 33/92; G01N 35/00584; G01N 35/026; G01N 35/1067; G01N 35/1074; G01N 35/1081; G01N 35/1095; G01N 37/00; G01N 9/24; G02B 21/32; G02B 21/0056; G02B 5/126; G02B 21/245; G02B 26/0875; G02B 26/101; G02B 3/0068; G02B 7/09; G02B 7/32; G02B 7/38; G02B 21/00; G02B 27/0012; G02B 27/1013; G02B 27/126; G02B 27/144; G02B 27/145; G02B 27/148; G02B 7/28; G02B 21/0088; G02B 21/365; G02B 21/367; A61L 2/0047; A61L 2/10; A61L 2202/11; A61L 2202/14; A61L 2202/23
See application file for complete search history.

(56) References Cited

U.S. PATENT DOCUMENTS

| | | | | |
|---|---|---|---|---|
| 6,979,073 | B2* | 12/2005 | Shrader | B41J 2/14008 347/46 |
| 7,218,810 | B2* | 5/2007 | Hillendahi | G01N 21/253 385/38 |
| 7,376,304 | B2* | 5/2008 | Hillendahi | G01N 21/6452 385/38 |
| 7,480,042 | B1 | 1/2009 | Phillips et al. | |
| 7,733,488 | B1* | 6/2010 | Johnson | G01J 3/02 356/414 |
| 8,591,836 | B2* | 11/2013 | Boege | B01L 3/50853 422/551 |
| 8,908,277 | B2 | 12/2014 | Pesach et al. | |
| 9,764,049 | B2 | 9/2017 | Eliason et al. | |
| 2007/0065074 | A1* | 3/2007 | Hillendahi | G01N 21/6452 385/33 |
| 2018/0059586 | A1 | 3/2018 | Kondo et al. | |
| 2018/0113066 | A1* | 4/2018 | Freitag | B01L 13/02 |

FOREIGN PATENT DOCUMENTS

| | | |
|---|---|---|
| KR | 20090010241 A | 1/2009 |
| WO | 2014058869 A1 | 4/2014 |
| WO | 2016054150 A1 | 4/2016 |
| WO | 2018080805 A1 | 5/2018 |

* cited by examiner

IRRADIATION SYSTEM FOR MULTIWELL INACTIVATION

CROSS REFERENCE TO RELATED APPLICATIONS

The present application is a continuation of U.S. Non-Provisional patent application Ser. No. 16/421,263 entitled "IRRADIATION SYSTEM FOR MULTIWELL INACTIVATION", and filed on May 23, 2019. U.S. Non-Provisional application Ser. No. 16/421,263 claims priority to U.S. Provisional Application No. 62/678,904 entitled "IRRADIATION SYSTEM FOR MULTIWELL INACTIVATION", and filed on May 31, 2018. The entire contents of each of the above-listed applications are hereby incorporated by reference for all purposes.

BACKGROUND AND SUMMARY

Ultraviolet germicidal irradiation (UVGI) is a disinfection method that uses short-wavelength ultraviolet (UV-C and/or UV-B) light to kill or inactivate microorganisms by disrupting their DNA. Ultraviolet germicidal irradiation is extensively used for sterilizing laboratory equipment and reagents, including microplates (also called multiwell, microwell, or microtiter plates). Microplates include a plurality of wells, each of the plurality of wells defined by a sidewall (or sidewalls) and a bottom of the plate and having a small volume capacity (e.g., 100-500 µL). Because the UV-B/C light must be in a direct line-of-sight with an area in order to disinfect it, microplates have been challenging to fully disinfect. For example, the sidewalls of each well may produce a shadowing effect and prevent the UV-B/C light from directly contacting areas of the well, such as the sidewall area close to the bottom of the well.

One example approach to address the above-mentioned problems includes including a plurality of UV-B/C light sources, such as in a 2D array, to provide complete coverage of the microplate and sufficient irradiance. However, including enough UV-B/C light sources to irradiate the entire microplate may be cost-prohibitive.

The inventors herein have recognized the above-mentioned issues and have engineered a way to at least partially address them. In one example approach, an irradiation system includes a plurality of light sources, each of the plurality of light sources included in a linear array and configured to emit radiation downward, relative to a vertical direction, toward an irradiation surface; an actuation system adapted to linearly move the linear array in an orthogonal direction, relative to the vertical direction; and one or more optical components positioned below, with respect to the vertical direction, the plurality of light sources. In this way, by linearly moving the linear array across the microplate and focusing the radiation emitted by the plurality of light sources via the one or more optical components, an entire microplate may be irradiated by a smaller number of light sources.

Furthermore, an example method includes focusing radiation emitted by an array of light sources on targeted regions of a microplate via an optical lens; and adjusting the targeted regions of the microplate by linearly moving the array of light sources across a width of the microplate, the width arranged in a direction of the linear movement. For example, a controller may adjust duration of irradiation in each of the targeted regions, and intensity of irradiation in each of the targeted regions, and a pattern of irradiation based on input from a user or according to a specified sterilization protocol.

In this way, deep UV irradiance with a single wavelength or a combination of multiple different wavelengths may be proved to a plurality of areas of a microplate, including the sidewall area close to the bottom of the well, with a greater than threshold intensity for at least a threshold duration, resulting in complete and effective sterilization of the targeted area. Furthermore, the illumination system may include economical optical components and a compact light source arrangement, which may reduce a cost and size of the UVGI system.

The above advantages, other advantages, and features of the present description will be readily apparent from the following detailed description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
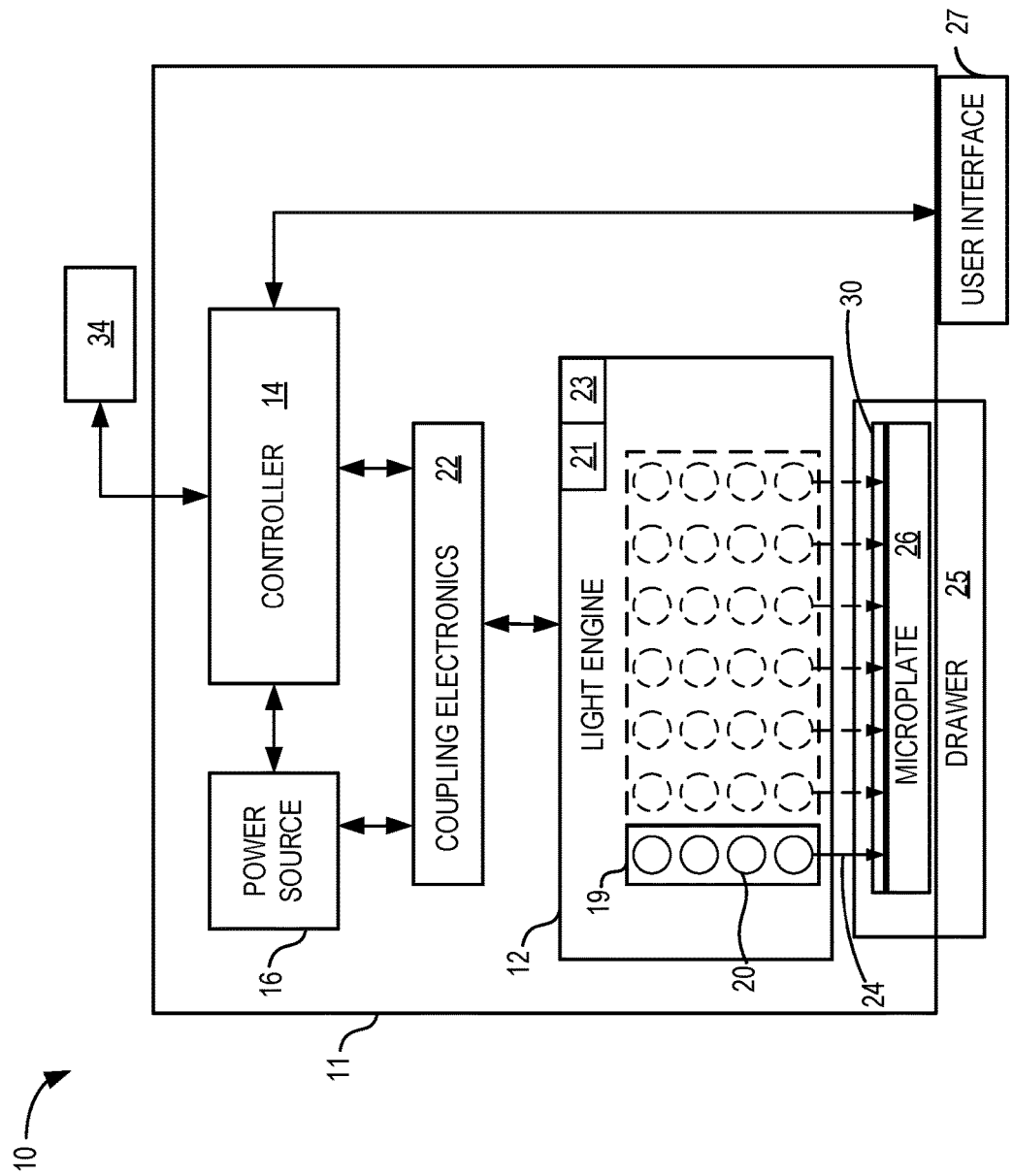
FIG. 1 illustrates a schematic of a microplate irradiation system.
Figure 8:
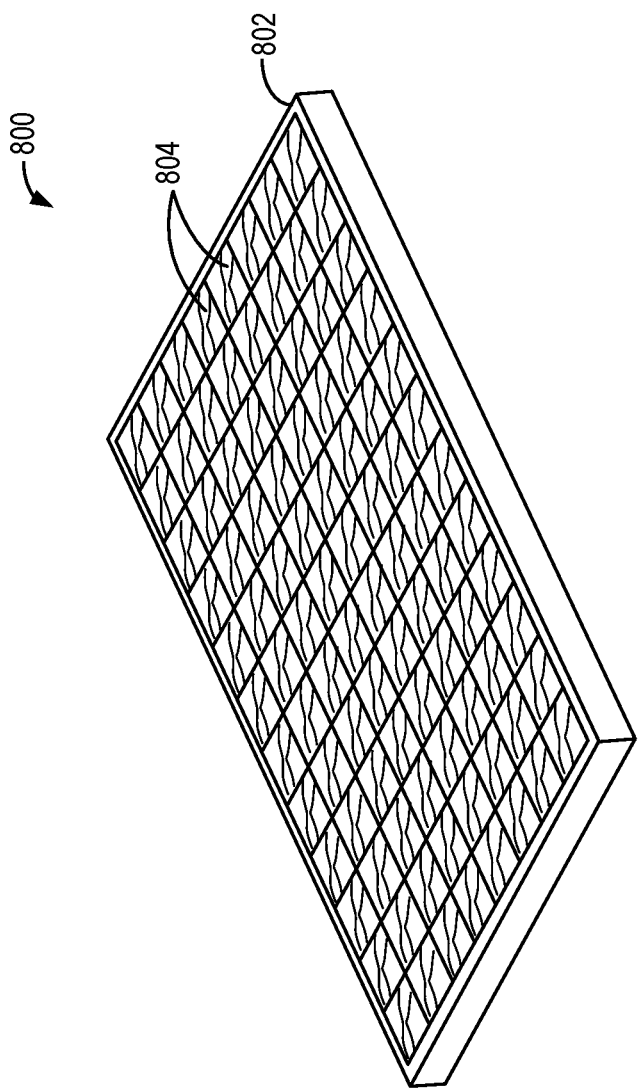
FIG. 8 shows an example array of Fresnel lenses included in a microplate cover.
Figure 9A:
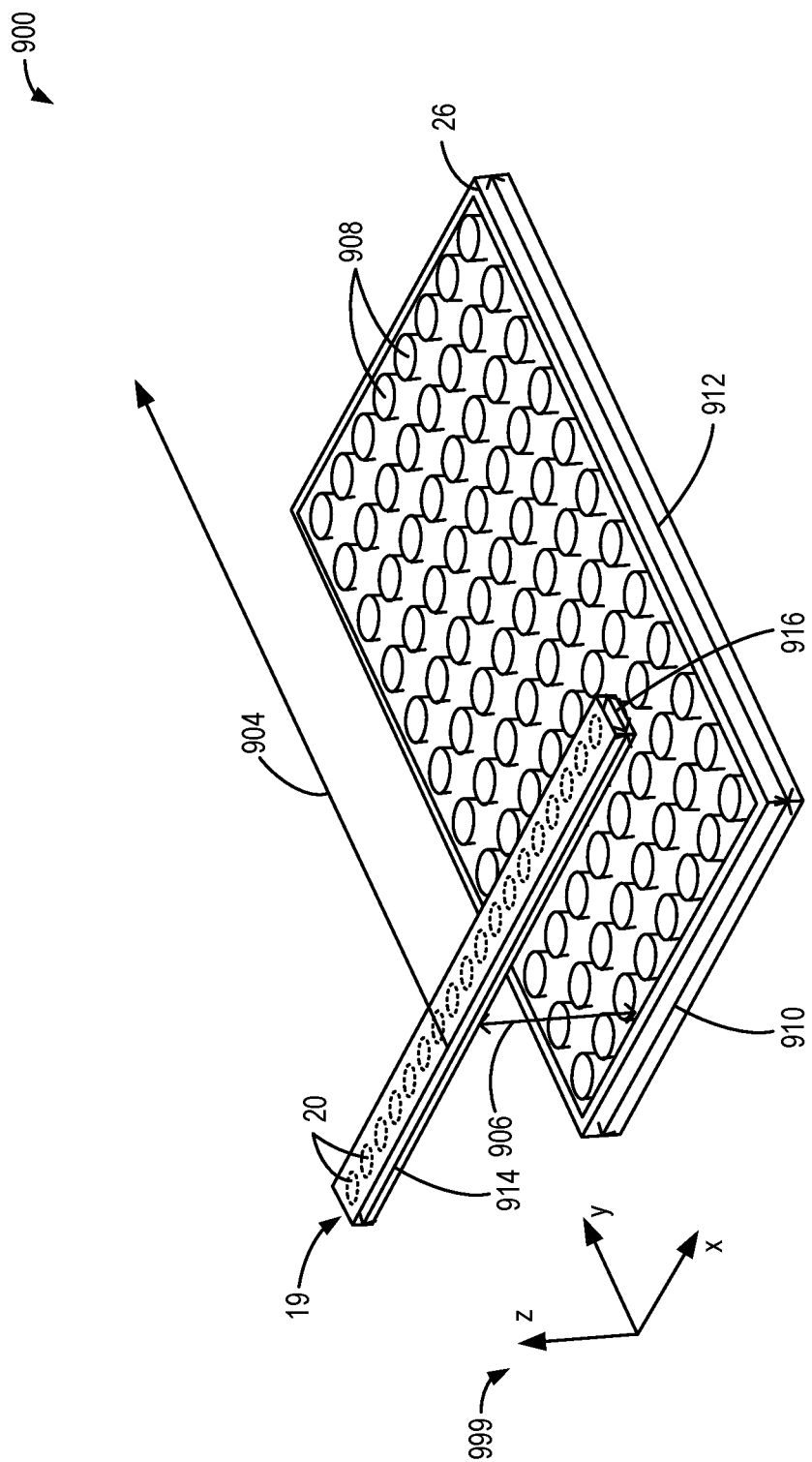
FIG. 9A shows an example linear array positioned over a microplate.
Figure 9C:
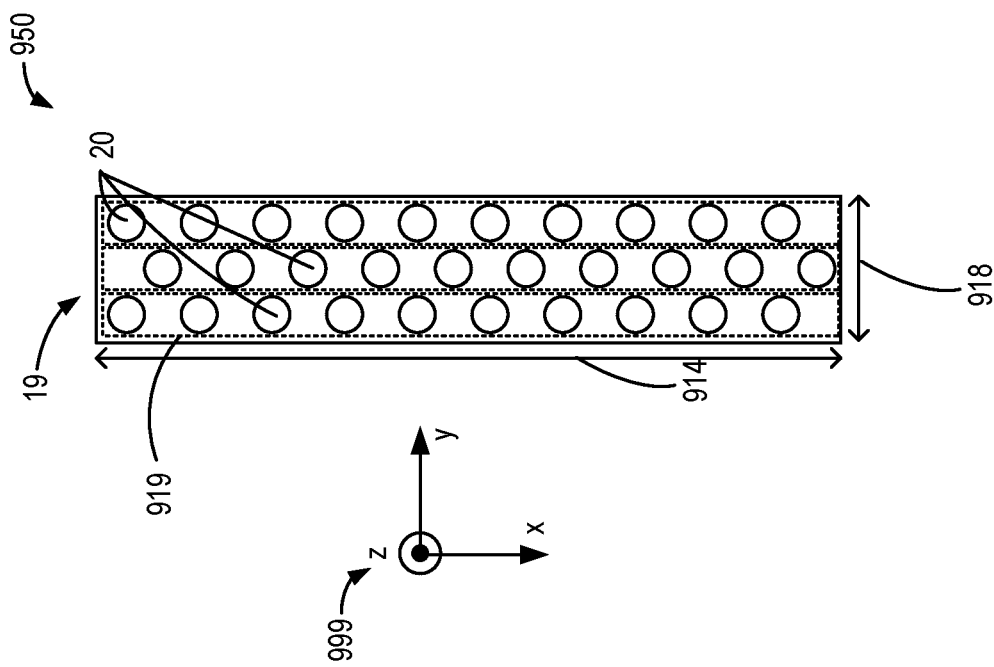
FIGS. 9B and 9C show alternative configurations of the linear array that may be positioned over the microplate in FIG. 9A.
Figure 9B:
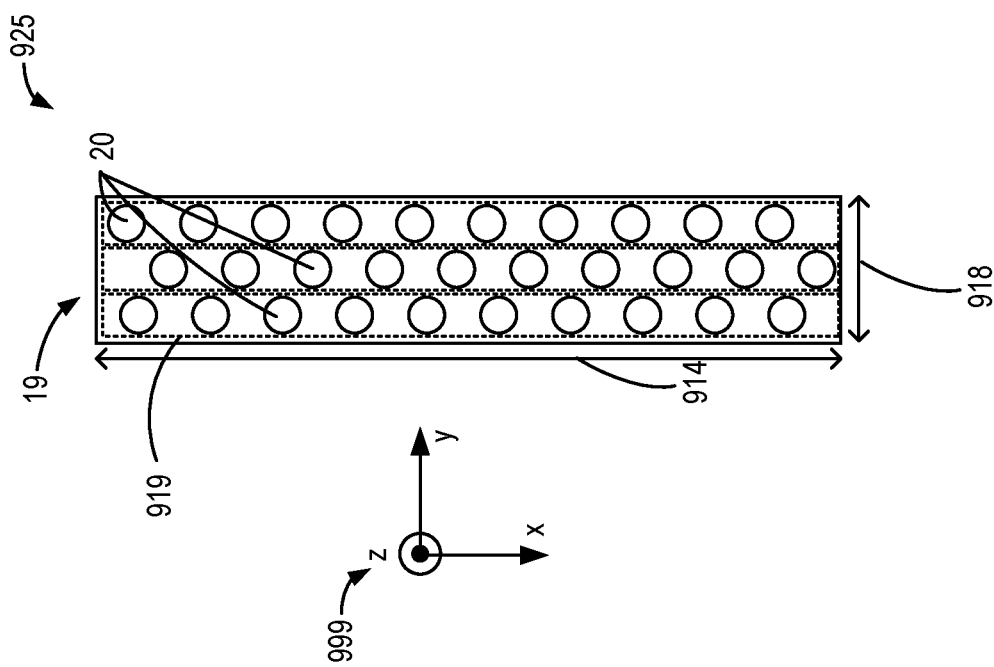

The present description relates to methods and systems for sterilizing a microplate using radiation, such as UV-B and/or UV-C radiation. FIG. 1 illustrates a schematic of a microplate irradiation system. An optical lens may be aligned with each well of the microplate, as shown in FIGS. 2A-2C, 3, and 5-7, and a linearly movable light source may scan across the wells to targetedly irradiate different areas of each well, as shown in FIGS. 2A-2C and FIG. 4. As an example, an array of lenses may be included in a microplate cover, as shown in FIG. 8, which may be positioned over the microplate prior to its insertion into the microplate irradiation system. Example configurations of a linear array of light sources that may scan across a width of a microplate are shown in FIGS. 9A-9C. A duration, intensity, and pattern of microplate irradiation may be regulated by a controller, such as according to the example method of FIG. 10.

Referring now to FIG. 1, a block diagram of an example configuration of a microplate irradiation system 10 is illustrated. The microplate irradiation system 10 may be used to emit radiation, such as UV light, infrared light, visible light, and/or other types of radiation. In one example, microplate irradiation system 10 may comprise a light engine 12, a controller 14, and a power source 16 contained within a housing 11.

The light engine 12 may include a linear array 19 of a plurality of light sources 20, as illustrated in FIG. 1. Each of light sources 20 may include one or more light emitting diodes (LEDs), for example. As another example, the light engine 12 may include a plurality of linear arrays 19 to form a two-dimensional array of light sources 20, or the linear array 19 may be a two-dimensional, multi-column array instead of a single-column array, as illustrated in dashes in FIG. 1. As a further example, the linear array 19 may include multiple linear subarrays, such as two or more linear subarrays arranged at an offset, as further illustrated with respect to FIGS. 9B and 9C. As shown in FIG. 1, the linear array 19 includes the plurality of light sources arranged in a line. Furthermore, the linear array may be longer in a first dimension than a second dimension (e.g., having a greater length than width), as further described below with respect to FIGS. 9A-9C. Light engine 12 may further include an actuation system 21 and a cooling system 23. For example, actuation system 21 may adjust a position of the linear array 19, such as by moving the linear array 19 in a linear scanning motion, such as in a direction of the shorter, second dimension, in order to irradiate different areas of the microplate 26, as will be further described with respect to FIGS. 2A-2C and FIGS. 7-10. As an example, actuation system 21 may include an electric motor that moves the linear array 19 or the microplate 26 relatively along a linear track. As one example, the linear array 19 may be moved along the linear track while the microplate 26 remains fixed in place. As another example, the microplate 26 may be moved along the linear track while the linear array 19 remains fixed in place. Cooling system 23 may include one or more temperature sensors, a forced air cooling system (e.g., a fan), a Peltier device, a heat sink, etc. that may be used to regulate a temperature of the light sources 20.

Each of the light sources 20 may provide radiant output 24. In one example, the radiant output 24 is UV-B/C radiation. The radiant output 24 may be directed to a microplate 26 positioned inside a drawer 25 inserted into the housing 11. In other examples, the microplate irradiation system 10 may be configured to hold other equipment or reagent-holding devices, such as microscope slides, tissue culture plates, etc., in addition to or alternatively to the microplate 26. Additionally, in alternative examples, instead of a drawer, the microplate irradiation system 10 may include an opening in the housing 11 accessible via a flap or door. Thus, when the flap or door is opened, a cavity within the housing 11 may be accessed via the opening, and the microplate 26 may be placed within the cavity. Thus, the drawer 25 (or cavity) may provide an irradiation surface. Furthermore, the radiant output 24 may be directed to the microplate 26 via one or more optical components 30. The optical components 30 may be variously implemented, as will be further described herein with respect to FIGS. 2A-2C and FIGS. 3-8. As an example, the optical components 30 may include one or more layers, materials or other structures, such as flat plates, ball lenses, Fresnel lenses, half-ball lenses, spherical lenses, aspherical lenses, etc. interposed between the light sources 20 and the microplate 26. The optical components 30 may be made from UV-transparent materials, such as fused silica, fused quartz, other glass, silicone, polymers, or other materials. The optical components 30 may serve to collect the radiant output 24 and/or direct the radiant output 24 to targeted areas of the microplate 26, as will be further described below with respect to FIGS. 2A-2C and FIG. 4.

Each of the layers, materials, or other structures of optical components 30 may have a selected index of refraction. By properly selecting each index of refraction, reflection at interfaces between layers, materials, and other structures in the path of the radiant output 24 may be selectively controlled (e.g., reduced).

The light engine 12, and therefore the linear array 19 and the plurality of light sources 20, may be coupled to the controller 14 via coupling electronics 22. For example, the light engine 12 may transmit signals to and receive signals from the coupling electronics 22 regarding a state of the plurality of light sources 20 (e.g., on and emitting radiation or off and not emitting radiation), a temperature of the plurality of light sources 20, a position of the linear array 19, etc., and the coupling electronics 22 may further communicate these signals to the controller 14. Furthermore, the controller 14 may transmit command signals to the coupling electronics 22 regarding a commanded state of the plurality of light sources, a commanded intensity of the radiant output 24, a commanded position of the linear array 19, etc., and the coupling electronics 22 may further communicate these signals to the light engine 12. In some examples, the irradiance at one or more locations at the microplate 26 surface may be detected by sensors (for example, sensors along the surface of the microplate 26, and/or sensors adjacent to the surface of the microplate 26) and transmitted to controller 14 in a feedback control scheme.

The power source 16 may be coupled to both of the controller 14 and the coupling electronics 22 to send and receive signals. As an example, in response to a command signal from controller 14 to turn the light sources 20 on, the power source 16 may supply power to the light engine 12 via the coupling electronics 22.

In addition to the power source 16 and the coupling electronics 22, the controller 14 may also be connected to a user interface 27 and an external device 34. The user interface 27 may include a display and an input device. As an example, the user interface 27 may be a touch screen display. The user interface 27 may enable a user of the microplate irradiation system 10 to access a programmable menu, the programmable menu including a duration of irradiation, an intensity and/or dose of irradiation, a pattern of irradiation, etc. The controller 14 may communicate to the external device 34 through one or more ports of the microplate irradiation system, such as a USB port, LAN port, etc. As another example, the controller 14 may communicate wirelessly with the external device 34, such as via a wireless internet connection, an infrared transponder, or a Bluetooth® link. The data received by the controller 14 from the user interface 27 and/or the external device 34 may be stored in a memory of the controller 14 and may be used to perform a programmed sterilization cycle, for example.

The controller 14 may receive data of various types from one or more of the power source 16, the coupling electronics 22, the external device 34, and/or the user interface 27. As an example, the data may be representative of one or more characteristics associated with the light sources 20. As another example, the data may be representative of one or more characteristics associated with the respective light engine 12, power source 16, user interface 27, and/or external device 34 providing the data. As still another example, the data may be representative of one or more characteristics associated with the microplate 26. Moreover, the data may be representative of some combination of these characteristics.

The controller 14, in receipt of any such data, may be implemented to respond to that data. For example, responsive to such data from any such component, the controller 14 may be implemented to control one or more of the power source 16, the light engine 12 (including the linear array 19 and/or one of more of the plurality of light sources 20), etc.

Individual LEDs of the plurality of light sources 20 of the light engine 12 may be controlled independently by controller 14. For example, controller 14 may control a first group of one or more individual LEDs to emit light of a first intensity, wavelength, and the like, while controlling a second group of one or more individual LEDs to emit light of a different intensity, wavelength, and the like. The first group of one or more individual LEDs may be within the same light source 20 of semiconductor devices or may be from more than one light source 20. Each of the plurality of light sources 20 of the light engine 12 may also be controlled independently by controller 14 from one another. For example, a first light source 20 including one or more LEDs may be controlled to emit light of a first intensity, wavelength, and the like, while those of a second light source 20 may be controlled to emit light of a second intensity, wavelength, and the like.

As described above, the microplate irradiation system 10 may be configured to receive the microplate 26 placed in the drawer 25 that may be inserted inside the housing 11 below the light engine. The microplate irradiation system 10 may also include a safety interlock system to activate and deactivate the light engine 12 when the drawer 25 is closed and opened, respectively.

The controller 14 may be an electronic controller and may include a memory storing instructions executable to carry out one or more of the methods described herein. The controller may include one or more physical logic devices, such as one or more processors, configured to execute the instructions. Additionally or alternatively, the controller may include hardware or firmware configured to carry out hardware or firmware instructions. The memory may include removable and/or built-in devices, including optical memory, semiconductor memory, and/or magnetic memory. The memory may include volatile, nonvolatile, dynamic, static, read/write, read-only, random-access, sequential-access, location-addressable, file-addressable, and/or content-addressable devices. The memory and logic device(s) may be integrated together into one or more hardware-logic components, such as field-programmable gate arrays (FPGAs).

As introduced above, the controller 14 may include instructions stored in non-transitory memory for linearly moving the linear array 19 (e.g., via the actuation system 21). For example, the linear array 19 (which may have a smaller overall surface area than the microplate 26, in one example) may be moved in an orthogonal direction relative to the microplate 26 in order to provide complete coverage of the microplate 26 with the radiant output 24. In particular, including a linearly movable linear array that is smaller than the microplate (or the object to be irradiated) reduces a number of the plurality of light sources 20 compared to when a two-dimensional array spanning the entire microplate is used, which reduces a cost of the microplate irradiation system 10. Furthermore, the scanning motion of the linear array 19 in combination with the optical components 30 enables the effective delivery of irradiation to niche areas, such as bottom corners of wells of the microplate 26. For example, due to a large incident angle of the radiant output 24 onto the niche areas, if the optical components 30 were not included, the irradiance to the niche area may be far less than needed for sterilization (the projected irradiance is proportional to the cosine of the incident angle). Therefore, by increasing the focused irradiance and introducing a larger slant angle via the optical components 30 and a positioning of the linear array 19, the microplate irradiation system 10 may achieve complete sterilization of the microplate 26.

Figure 2A:
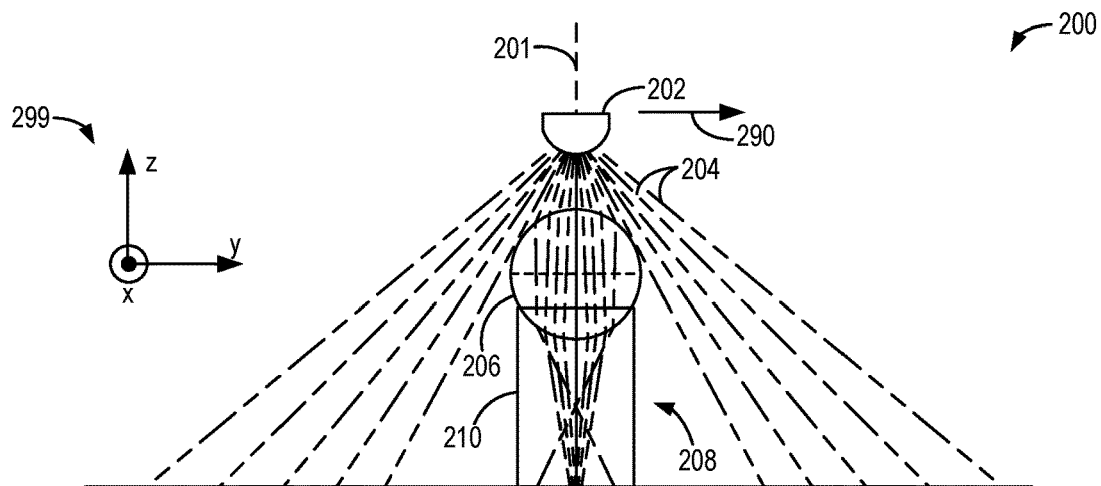
FIGS. 2A-2C show an example of scanning a single well of a microplate with a linearly moveable light source and a ball lens for focusing the light source radiant output.
Figure 2B:
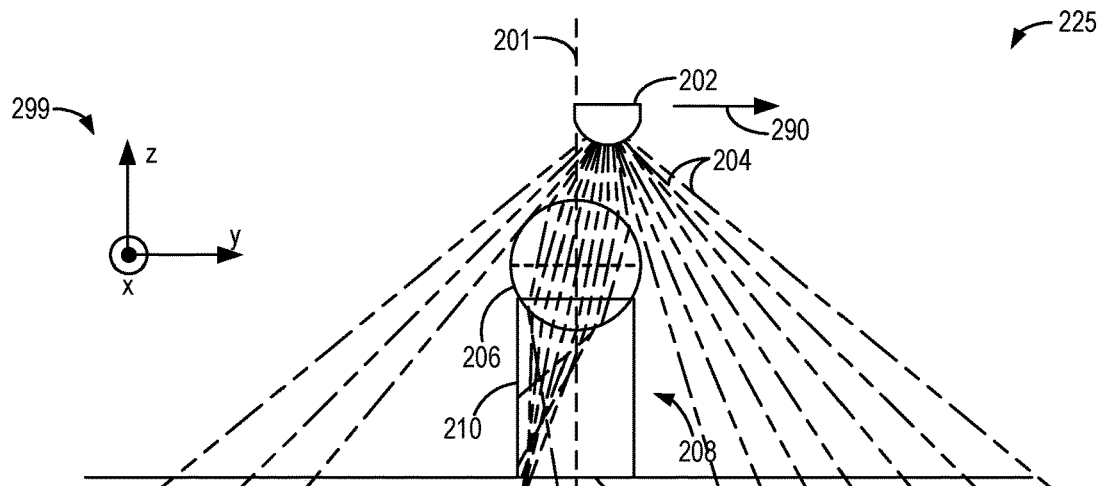
Figure 2C:
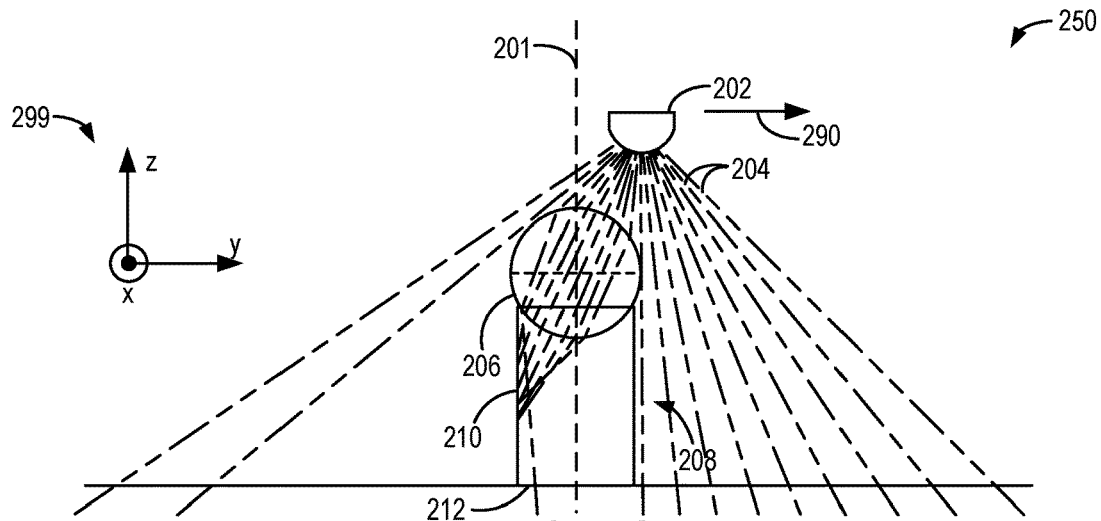

As a simplified example, scanning a single well of a microplate with a linearly moveable light source and an optical component for focusing the light source radiant output is shown in FIGS. 2A-2C. In particular, as the light source is linearly moved, a targeted region of high intensity irradiation within the well changes. The views shown in FIGS. 2A-2C are in the y-z plane, as indicated by reference axes 299, and are two-dimensional representations of three-dimensional objects.

FIGS. 2A-2C show a light source 202 positioned over a well 208. The light source 202 may be one of the plurality of light sources 20 shown in FIG. 1, and the well 208 may be included in the multiwell plate 26 shown in FIG. 1. The light source 202, which may be an LED, is linearly movable in the y-direction, as indicated by a scanning direction 290, and emits light (e.g., radiant output 24 shown in FIG. 1, which may be UV-B/C light) in a plurality of light paths 204. As an example, an individual element of light source 202 may be an exposed LED die or an encapsulated LED die with a lens or reflector in the proximity of the die. The well 208 includes a sidewall 210 and a bottom 212. The sidewall 210 may be approximately perpendicular to the bottom 212 and couple to the bottom 212 at a junction. As an example, the well 208 may be a hollow cylinder open at a top end and closed at the bottom 212, although other geometries are also possible. Therefore, the sidewall 210 may be a continuous, cylindrical piece.

A spherical ball lens 206 is positioned between the well 208 and the light source 202, such as within a top opening of the well 208. For example, a diameter of ball lens 206 may be greater than a diameter of the well 208, allowing ball lens 206 to rest atop well 208 and partially protrude into well 208. Most non-coherent light sources, such as LEDs, have wide emission angles, which is challenging to collect at high efficiency. However, the ball lens 206 efficiently collects the wide-angle emissions from the light source 202 while also providing a compact optical system due to its short back focal distance. Additionally, the spherical symmetry of the ball lens 206 enables omnidirectional incidence for light sources located at various locations, such as if more than one light source 202 is provided (as further illustrated herein with respect to FIG. 7).

FIG. 2A shows a first view 200 in which light source 202 is aligned with ball lens 206 and well 208 along a symmetric axis 201 of the well 208. With the light source 202 aligned along the symmetric axis 201, the light paths 204 emitted by the light source 202 that pass through the ball lens 206 are focused at the bottom 212 of the well 208, particularly along the symmetric axis 201. Therefore, with the light source 202 aligned along the symmetric axis 201, the bottom 212 of the well 208 may be irradiated with high intensity.

FIG. 2B shows a second view 225 in which light source 202 has been linearly translated in the scanning direction 290 to a first position that is off of the symmetric axis 201. With the light source 202 in the first position and no longer aligned with the symmetric axis 201, the light paths 204 emitted by the light source 202 that pass through the ball lens 206 are focused at the bottom 212 of the well 208 near the sidewall 210 and on the sidewall 210 near the bottom 212. That is, the ball lens 206 directs the light emitted by light source 202 with a larger slant angle to increase irradiance at the junction where the bottom 212 and the sidewall 210 of the well 208 meet. Therefore, with the light source 202 in the first position, the bottom 212 is no longer irradiated with high intensity along the symmetric axis 201, as in the first view 200. Instead, the bottom 212 near the sidewall 210 may be irradiated with high intensity.

FIG. 2C shows a third view 250 in which light source 202 has been linearly translated in the scanning direction 290 to a second position that is farther off of (e.g., away from) the symmetric axis 201 than the first position shown in second view 225. With the light source 202 in the second position, the light paths 204 emitted by the light source 202 that pass through the ball lens 206 are focused at the sidewall 210 farther from the bottom 212, such as close to the opening of the well. That is, the ball lens 206 directs the light emitted by light source 202 with an even larger slant angle than when the light source 202 is in the first position shown in second view 225 to increase irradiance along the sidewall 210. Therefore, with the light source 202 in the second position, the bottom 212 is no longer irradiated, and the sidewall 210 near the middle of the well (in the z-direction) and the top of the well (in the z-direction) may be irradiated with high intensity.

Although first view 200, second view 225, and third view 250 show three light source positions, it should be understood that light source 202 may be positioned in other locations in the y-direction during the scanning. For example, the light source 202 may be positioned to the left of the symmetric axis 201 (e.g., in the opposite direction of scanning direction 290) so that an opposite side of the sidewall 210 may be irradiated. As another example, the light source 202 may pause at any number of y-direction locations between the symmetric axis 201 and the second position. As still another example, the light source 202 may continue to be linearly translated beyond the second location in the scanning direction 290.

Figure 3:
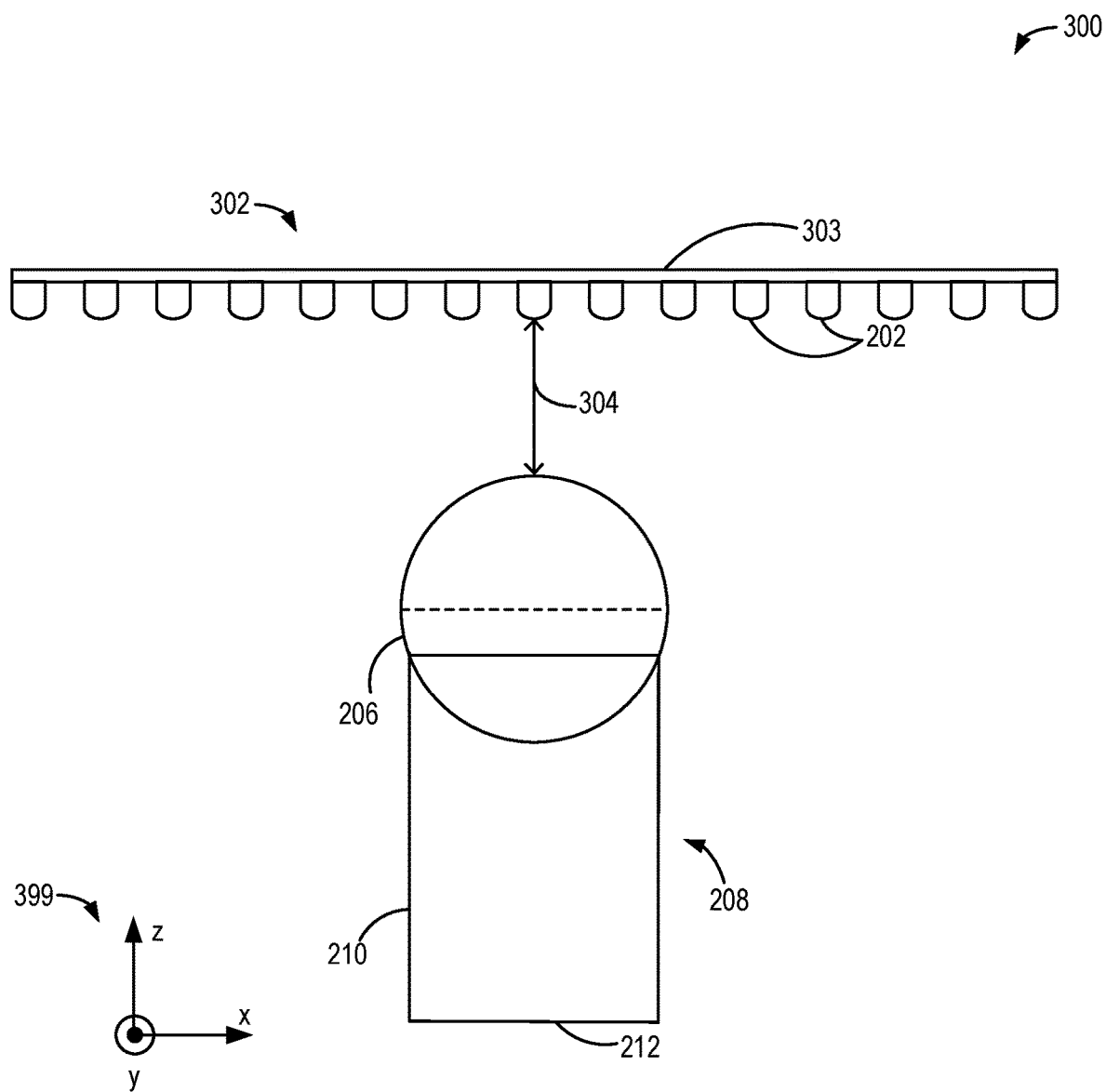
FIG. 3 shows an example of a linearly moveable linear light source array for scanning a single well of a microplate.

Although the simplified examples shown in FIGS. 2A-2C show a single light source for illuminating a single well of a microplate, a linear light source array may be provided to provide a complete irradiation of the curved inner surface of the sidewall. Therefore, FIG. 3 schematically shows an example configuration 300 of a linear light source array 302 with respect to the well 208 and the ball lens 206 introduced in FIGS. 2A-2C. Components previously introduced in FIGS. 2A-2C are numbered the same and may not be reintroduced. The linear light source array 302 may be included in a light engine, such as the linear array 19 included in the light engine 12 shown in FIG. 1, for example, so that the linear light source array 302 may be actuated in the y-direction (with respect reference axes 399) in order to target different locations of the well 208. The view shown in FIG. 3 is in the x-z plane, as indicated by the reference axes 399, and is a two-dimensional representation of three-dimensional objects, as described above with respect to FIGS. 2A-2C.

The linear light source array 302 includes a plurality of light sources 202 coupled to a substrate 303. Actuation of the substrate 303 (e.g., by the actuation system 21 shown in FIG. 1) moves the plurality of light sources 202 in concert. The plurality of light sources 202 may emit the same or different wavelength of electromagnetic radiation (e.g., UV-B/C light) at the same or different intensities. As a non-limiting example, the linear light source array 302 may include fifteen 1×1 $mm^2$ LEDs distributed in x-direction at a pitch of 1.2 mm. The linear light source array 302 may scan across the well 208 in the y-direction. Thus, the linear light source array 302 may be fixed in both the x-direction and the z-direction. However, in other examples, the linear light source array 302 may be raised or lowered (e.g., in the z-direction) or translated in the x-direction prior to the scanning.

The ball lens 206 is positioned on top of the well 208, as in FIGS. 2A-2C. As a non-limiting example, the cylindrical well 208 may have a diameter of 7.5 mm and a height of 11 mm, and the ball lens 206 may be a fused silica ball lens with a diameter of 8 mm. The linear light source array 302 may be positioned at a distance 304 above the ball lens 206. As a non-limiting example, the distance 304 may be 5 mm. Thus, the linear light source array 302 and the ball lens 206 are spaced apart in the vertical (e.g., z-axis) direction. The distance 304 may be calibrated such that the ball lens 206 may efficiently collect light from the plurality of light sources 202 and efficiently focus the light to provide a desired irradiance intensity to targeted areas of the well 208. As an example, if the ball lens 206 were not included in the example configuration 300, the resulting irradiation intensity may be reduced at least 10-fold.

Figure 4:
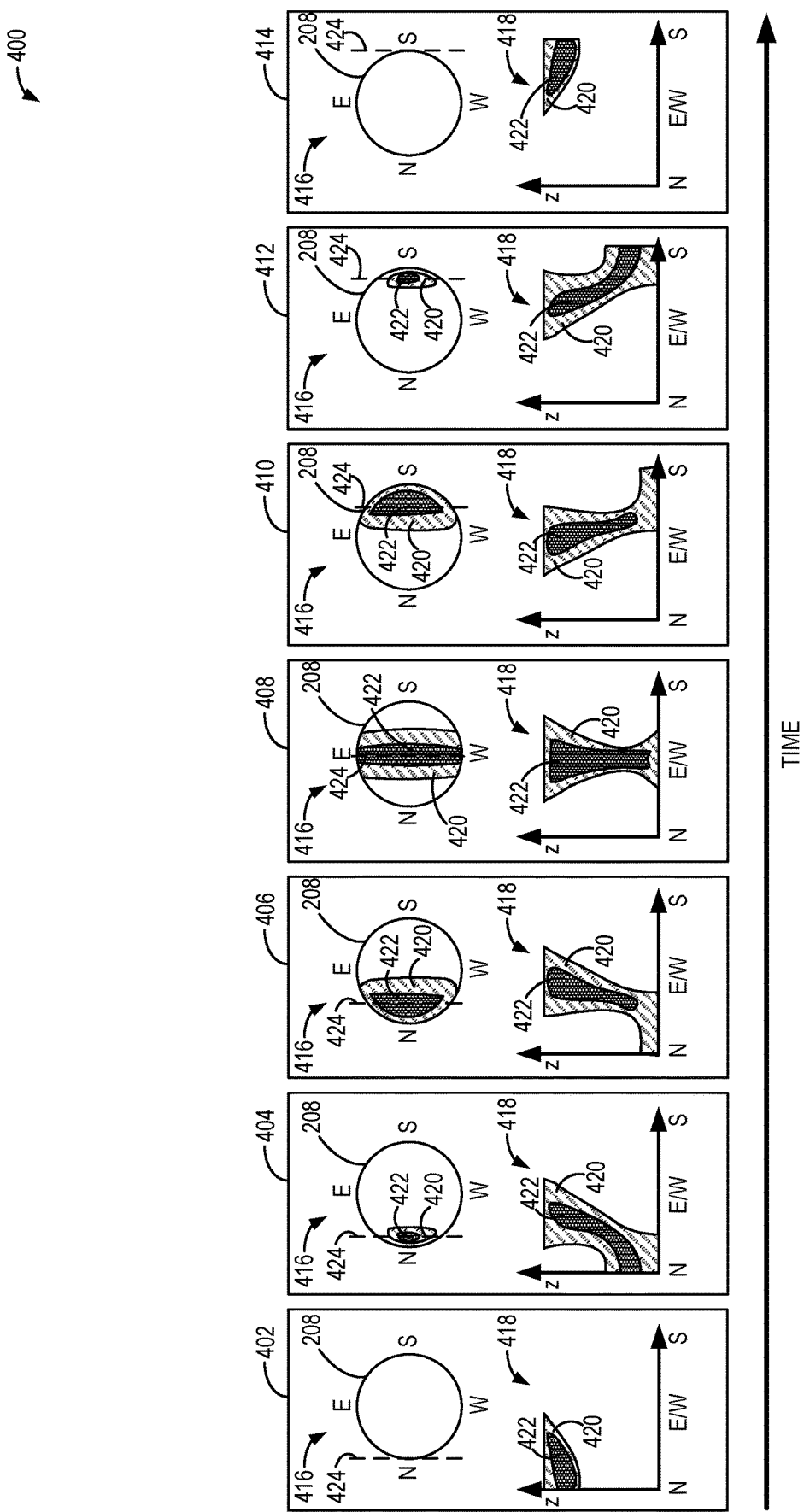
FIG. 4 shows example irradiation pattern on a bottom and a sidewall of a single well of a microplate during scanning of a linear light source array.

FIG. 4 shows an example time lapse 400 of scanning a linear light source array (e.g., the linear light source array 302 of FIG. 3) in the y-direction (with respect to reference axes 399 shown in FIG. 3) to targetedly irradiate different areas of the well 208 introduced in FIGS. 2A-2C and 3 with high intensity irradiation via an optical lens (e.g., ball lens 206 shown in FIGS. 2A-2C and 3). The time lapse 400 includes a plurality of frames 402, 404, 406, 408, 410, 412, and 414, with each frame including an overhead view 416 looking down into the well 208 (e.g., in the x-y plane with respect to reference axes 399 shown in FIG. 3). Each overhead view 416 shows irradiation targeted to a bottom of the well (e.g., bottom 212 of FIGS. 2A-2C and 3). Reference points of the well 208 are labeled as N ("north"), S ("south"), E ("east"), and W ("west"). Each frame further includes a graph 418 showing irradiation targeted to a sidewall of the well (e.g., sidewall 210 of FIGS. 2A-2C and 3). The horizontal axis of each graph 418 shows a horizontal position of the sidewall with respect to the north, south, east, and west reference points. Since the well 208 is symmetrical, E and W occur at the same horizontal position. The vertical axis represents a height of the sidewall (e.g., in the z-direction, with respect to reference axes 399 shown in FIG. 3). In each of the overhead views 416 and the graphs 418, a first, diagonally shaded region 420 shows areas of the well that are being irradiated. A second shaded region 422 shows areas of the well receiving higher intensity irradiation, such as where the irradiation is maximal. Furthermore, the scanning direction of the linear light source array is from north to south.

In a first frame 402, which corresponds to an earliest time, the linear light source array is in a first, north-most position (e.g., having a smallest y-value with respect to reference axes 399 shown in FIG. 3), as indicated by a dashed line 424. With the linear light source array at the first position, radiant output from a plurality of light sources of the linear light source array does not appreciably reach the bottom of the well. Therefore, overhead view 416 does not include region 420 or region 422. Instead of reaching the bottom of the well, the light emitted by the plurality of light sources is focused on upper north, northeast, and northwest portions of the sidewall, as shown by region 420 and region 422 in graph 418.

In a second frame 404, which is captured after the first frame 402, the linear light source array has moved to a second, further south position compared with first frame 402, as indicated by the dashed line 424. With the linear light source array at the second position, radiant output from the plurality of light sources of the linear light source array illuminates a relatively north section of the bottom of the well, as shown by region 420 and region 422 in overhead view 416. However, a majority of the radiant output is focused on the sidewall, as shown by region 420 and region 422 in graph 418. With the linear light source array at the second position, the mid-to-low north region of the sidewall and the upper northeast and northwest regions of the sidewall are irradiated.

In a third frame 406, which is captured after the second frame 404, the linear light source array has moved to a third, further south position compared with second frame 404, as indicated by the dashed line 424. With the linear light source array at the third position, radiant output from the plurality of light sources of the linear light source array illuminates north, northwest, and northeast areas of the bottom of the well, as shown by region 420 and region 422 in overhead view 416. Additional radiant output is focused on the sidewall, as shown by region 420 and region 422 in graph 418. With the linear light source array at the third position, the irradiation continues to reach the bottom north section of the sidewall, but the higher intensity irradiation shown by region 422 has moved further east and west.

In a fourth frame 408, which is captured after the third frame 406, the linear light source array has moved to a fourth position that is mid-way between north and south, as indicated by the dashed line 424. With the linear light source array at the fourth position, radiant output from the plurality of light sources of the linear light source array illuminates east-northeast, east, east-southeast, west-northwest, west, and west-southwest areas of the bottom of the well, as shown by region 420 and region 422 in overhead view 416. The highest intensity irradiation is focused in an area that spans from east to west, as shown by region 422. The sidewall also receives irradiation, as shown by region 420 and region 422 in graph 418. With the linear light source array at the fourth position, the irradiation continues to reach the bottom east and west sections of the sidewall, and the highest intensity irradiation shown by region 422 is focused on the mid-to-upper east and west regions of the sidewall.

In a fifth frame 410, which is captured after the fourth frame 408, the linear light source array has moved to a fifth, further south position compared with fourth frame 408, as indicated by the dashed line 424. With the linear light source array at the fifth position, radiant output from the plurality of light sources of the linear light source array illuminates south, southwest, and southeast areas of the bottom of the well, as shown by region 420 and region 422 in overhead view 416. Additional radiant output is focused on the sidewall, as shown by region 420 and region 422 in graph 418. With the linear light source array at the fifth position, the irradiation reaches the bottom south section of the sidewall, with the higher intensity irradiation shown by region 422 focused on mid-to-upper east, southeast, west, and southwest regions.

In a sixth frame 412, which is captured after the fifth frame 410, the linear light source array has moved to a sixth, further south position compared with fifth frame 410, as indicated by the dashed line 424. With the linear light source array at the sixth position, radiant output from the plurality of light sources of the linear light source array illuminates a relatively south section of the bottom of the well, as shown by region 420 and region 422 in overhead view 416. However, a majority of the radiant output is focused on the sidewall, as shown by region 420 and region 422 in graph 418. With the linear light source array at the sixth position, the mid-to-low south region of the sidewall and the upper southeast and southwest regions of the sidewall are irradiated.

In a seventh frame 414, which corresponds to a latest time in the time lapse 400, the linear light source array is in a seventh, south-most position (e.g., having a largest y-value with respect to reference axes 399 shown in FIG. 3), as indicated by dashed line 424. With the linear light source array at the seventh position, radiant output from the plurality of light sources of the linear light source array does not appreciably reach the bottom of the well. Therefore, overhead view 416 does not include region 420 or region 422. Instead of reaching the bottom of the well, the light emitted by the plurality of light sources is focused on upper south, southwest, and southeast portions of the sidewall, as shown by region 420 and region 422 in graph 418.

Thus, as the linear light source array scans from north to south, the irradiance focused on the bottom circular portion of the well by the ball lens also moves from north to south. Furthermore, the irradiance focused on the cylindrical sidewall by the ball lens moves similar to a windshield wiper across a windshield, from the north section, across the east and west regions, and finally to the south region. It should be understood that the frames represent example peak irradiance snapshots. Furthermore, a plurality of additional positions may be present between each of the first, second, third, fourth, fifth, sixth, and seventh positions.

Figure 5:
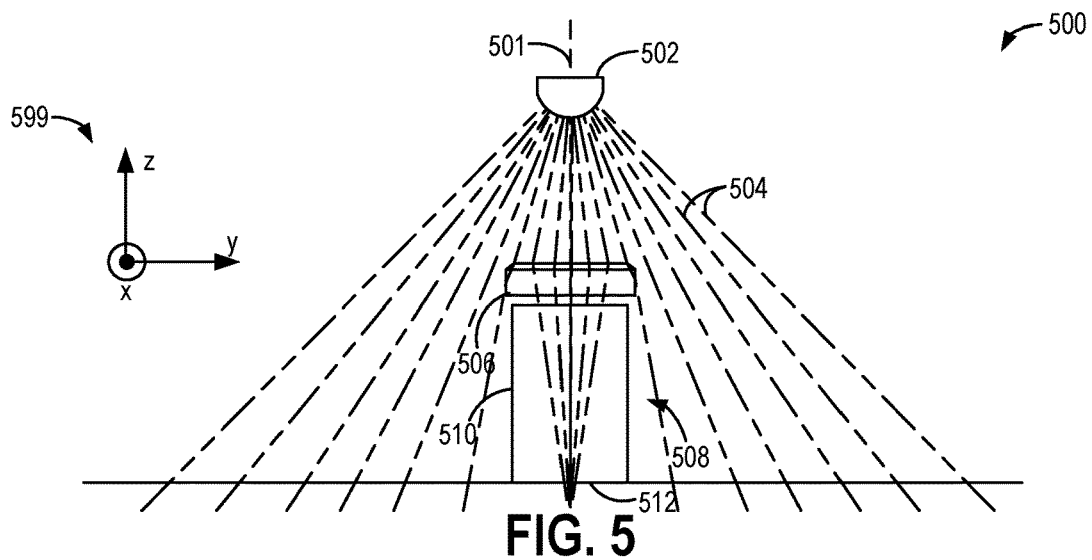
FIG. 5 shows an example of a Fresnel lens for focusing the light source radiant output within a single well of a microplate.

In other examples of the microplate irradiation system shown in FIG. 1, other focusing lenses may be included in the optical components coupled between the light source and the well. As one example, FIG. 5 shows a view 500 of a light source 502 positioned over a well 508. The light source 502 may be one of the plurality of light sources 20 shown in FIG. 1, and the well 508 may be included in the multiwell plate 26 shown in FIG. 1. The light source 502, which may be an LED, is linearly movable in the y-direction with respect to reference axes 599, and emits light (e.g., radiant output 24 shown in FIG. 1, which may be UV-B/C light) in a plurality of light paths 504. An individual element of light source 502 may be an exposed LED die or an encapsulated LED die with a lens or reflector in the proximity of the die. Similar to the well 208 described with respect to FIGS. 2A-2C, the well 508 includes a sidewall 510 and a bottom 512. The sidewall 510 may be approximately perpendicular to the bottom 512 and couple to the bottom 512 at a junction. As an example, the well 508 may be a hollow cylinder open at a top end and closed at the bottom 512, although other geometries are also possible. Therefore, the sidewall 510 may be a continuous, cylindrical piece.

A Fresnel lens 506 is positioned between the well 508 and the light source 502, such as over a top opening of the well 508. For example, a diameter of Fresnel lens 506 may be greater than a diameter of the well 508, allowing Fresnel lens 506 to rest atop well 508. In some examples, a flat plate may be included between the Fresnel lens 506 and the well 508. Furthermore, in some examples, a standard lens may be included in place of the Fresnel lens 506. However, the Fresnel lens 506 may be selected over the standard lens as it may function similarly but with reduced material absorption due to its reduced thickness and compact format.

When the light source 502 is positioned aligned with a symmetric axis 501 of the well 508, the Fresnel lens 506 efficiently collects the wide-angle emissions from the light source 502 and focuses the light paths 504 on a bottom 512 of the well 508 along the symmetric axis 501, similar to ball lens 206 in view 200 shown in FIG. 2A. Therefore, as the light source 502 linearly moves in the y-direction (not shown), Fresnel lens 506 may focus irradiation from the light source 502 on different locations of the well 508, similar to ball lens 206 shown in FIGS. 2A-2C. Therefore, Fresnel lens 506 serves as an alternative to ball lens 206 of FIGS. 2A-2C and may help facilitate formation of an array of lenses on a flat, UV-transparent substrate, as will be further described below with respect to FIG. 8. Example advantages of using Fresnel lens 506 include reduced lens weight and UV absorption by the material due to the reduced (e.g., shortened) lens thickness, its ability to be integrated into a lens array, and its reduced production cost. However, a front focal length of Fresnel lens 506 is longer than that off ball lens 206, which extends a standoff distance between the Fresnel lens 506 and the light source 502 (compared with a standoff distance between ball lens 206 and light source 202 of FIGS. 2A-2C) and may reduce the light collection efficiency.

Figure 6:
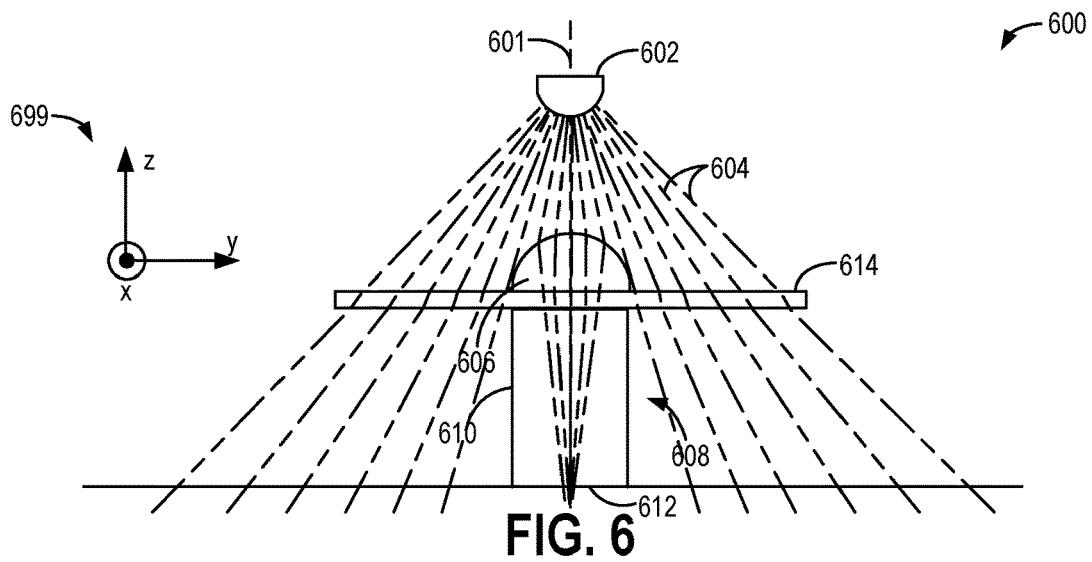
FIG. 6 shows an example of a half-ball lens for focusing the light source radiant output within a single well of a microplate.

As another example, FIG. 6 shows a view 600 of a light source 602 positioned over a well 608. The light source 602 may be one of the plurality of light sources 20 shown in FIG. 1, and the well 608 may be included in the multiwell plate 26 shown in FIG. 1. The light source 602, which may be an LED, is linearly movable in the y-direction with respect to reference axes 699, and emits light (e.g., radiant output 24 shown in FIG. 1, which may be UV-B/C light) in a plurality of light paths 604. An individual element of light source 602 may be an exposed LED die or an encapsulated LED die with a lens or reflector in the proximity of the die. Similar to the well 208 described above with respect to FIGS. 2A-2C and the well 508 described above with respect to FIG. 5, the well 608 includes a sidewall 610 and a bottom 612. The sidewall 610 may be approximately perpendicular to the bottom 612 and may couple to the bottom 612 at a junction. As an example, the well 608 may be a hollow cylinder open at a top end and closed at the bottom 612, although other geometries are also possible. Therefore, the sidewall 610 may be a continuous, cylindrical piece.

A half-ball lens 606 is positioned between the well 608 and the light source 602 atop a flat plate 614. The flat plate 614 is shown positioned on top of the well 608. In some examples, the flat plate 614 may span across a plurality of wells in addition to the well 608 and may include a plurality of half-ball lenses positioned thereon, such as aligned with a symmetric axis of each well. The flat plate 614 may be comprised of UV-transparent materials so that the UV-B/C light emitted by the light source 602 is transmitted through the flat plate 614 and is not absorbed or reflected by the flat plate 614. As an example, the half-ball lens 606 may be fused or bonded to the flat plate 614, which may hold the half-ball lens 606 fixedly in place for precise optical alignment with a symmetric axis 601 of the well 608.

When the light source 602 is positioned aligned with the symmetric axis, the half-ball lens 606 efficiently collects the wide-angle emissions from the light source 602 and focuses the light paths 604 on a bottom 612 of the well 608 along the symmetric axis 601, similar to ball lens 206 in view 200 shown in FIG. 2A. Therefore, as the light source 602 linearly moves in the y-direction (not shown), half-ball lens 606 may focus irradiation from the light source 602 on different locations of the well 608, similar to ball lens 206 shown in FIGS. 2A-2C. Therefore, half-ball lens 606 serves as an alternative to ball lens 206 of FIGS. 2A-2C and may help facilitate formation of an array of lenses on a flat, UV-transparent substrate (e.g., flat plate 614), as will be further described below with respect to FIG. 8. For example, the half-ball lens 606 may be fused to a common transparent substrate that covers the entire microplate, so that the array of lenses may be fabricated in an economic fashion.

Figure 7:
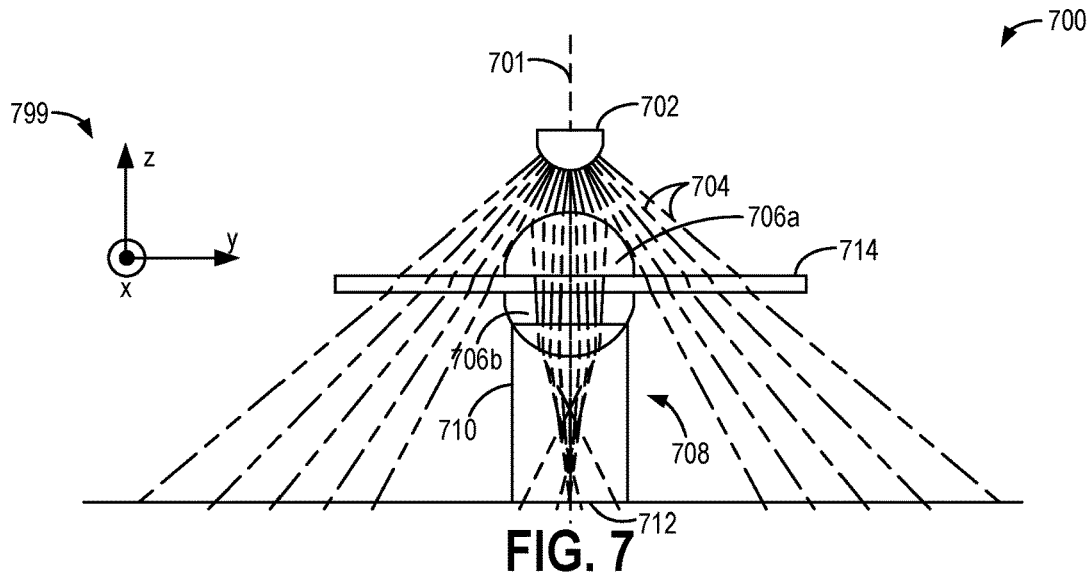
FIG. 7 shows an example of two half-ball lenses for focusing the light source radiant output within a single well of a microplate.

As another example, FIG. 7 shows a view 700 of a light source 702 positioned over a well 708. The light source 702 may be one of the plurality of light sources 20 shown in FIG. 1, and the well 708 may be included in the multiwell plate 26 shown in FIG. 1. The light source 702, which may be an LED, is linearly movable in the y-direction with respect to reference axes 799, and emits light (e.g., radiant output 24 shown in FIG. 1, which may be UV-B/C light) in a plurality of light paths 704. An individual element of light source 702 may be an exposed LED die or an encapsulated LED die with a lens or reflector in the proximity of the die. Similar to the well 208 described above with respect to FIGS. 2A-2C, the well 508 of FIG. 5, and the well 608 of FIG. 6, the well 708 includes a sidewall 710 and a bottom 712. The sidewall 710 may be approximately perpendicular to the bottom 712 and may couple to the bottom 712 at a junction. As an example, the well 708 may be a hollow cylinder open at a top end and closed at the bottom 712, although other geometries are also possible. Therefore, the sidewall 710 may be a continuous, cylindrical piece.

Two half-ball lenses are positioned between the well 708 and the light source 702. As shown in FIG. 7, a first half-ball lens 706a is positioned atop a flat plate 714, and a second half-ball lens 706b is positioned below the flat plate 714 and atop the well 708, such that the flat plate 714 is sandwiched between the two half-ball lenses. The flat plate 714 may be comprised of UV-transparent materials so that the UV-B/C light emitted by the light source 702 is transmitted through the flat plate 714 and is not absorbed or reflected by the flat plate 714. In some examples, the flat plate 714 may span across a plurality of wells in addition to the well 708 and may include a plurality of first half-ball lenses positioned thereon and a plurality of half-ball lenses positioned underneath, such as aligned with a symmetric axis of each well. As an example, each of the first half-ball lens 706a and the second half-ball lens 706b may be fused or bonded to the flat plate 714, which may hold the first half-ball lens 706a and the second half-ball lens 706b fixedly in place for precise optical alignment with a symmetric axis 701 of the well 708. The first half-ball lens 706a and the second half-ball lens 706b are symmetrically aligned, such as aligned with the symmetric axis, and are vertically reflected (e.g., in the z-direction) with respect to one another. Therefore, the two half-ball lenses in the combination shown in view 700 may more closely approximate ball lens 206 shown in FIGS. 2A-2C than the Fresnel lens 506 shown in FIG. 5 or the half-ball lens 606 shown in FIG. 6.

When the light source 702 is positioned aligned with the symmetric axis, the first half-ball lens 706a and the second half-ball lens 706b efficiently collect the wide-angle emissions from the light source 702 and focus the light paths 704 on a bottom 712 of the well 708 along the symmetric axis 701, similar to ball lens 206 in view 200 shown in FIG. 2A. Therefore, as the light source 702 linearly moves in the y-direction (not shown), the first half-ball lens 706a and the second half-ball lens 706b may focus irradiation from the light source 702 on different locations of the well 708, similar to ball lens 206 shown in FIGS. 2A-2C. Therefore, the first half-ball lens 706a and the second half-ball lens 706b serve as an alternative to ball lens 206 of FIGS. 2A-2C and may help facilitate formation of an array of lenses on a flat, UV-transparent substrate (e.g., flat plate 714), as will be further described below. For example, by using two half-ball lenses 706a and 706b fused on a common transparent substrate, the array of lenses may be fabricated in an economic fashion. Furthermore, the pair of half-ball lenses provides a much shorter front focal distance than the ball lens 206 of FIGS. 2A-2C, the Fresnel lens 506 of FIG. 5, and the single half-ball lens 606 of FIG. 6 so that the light source may be positioned closer to the array of lenses to increase the light collection efficiency.

Turning now to FIG. 8, an example Fresnel lens microplate cover 800 is shown. The Fresnel lens microplate cover 800 includes a plurality of Fresnel lenses 804 arranged in a two-dimensional array within a lid substrate 802. The Fresnel lenses 804 may correspond to the Fresnel lens 506 of FIG. 5, for example. Specifically, the Fresnel lens microplate cover 800 may be configured to cover and/or seal a microplate, which may be microplate 26 of FIG. 1, as well as provide focusing capability for one or more light sources (e.g., the plurality of light sources 20 shown in FIG. 1). Although the example of FIG. 8 includes Fresnel lenses, in other examples, other types of lenses may be alternatively included, such as standard lenses, half-ball lenses (e.g., half-ball lens 606 shown in FIG. 6), or two half-ball lenses (e.g., first half ball lens 706a and second half ball lens 706b shown in FIG. 7).

The example Fresnel lens microplate cover 800 shown in FIG. 8 includes 96 Fresnel lenses 804 in an eight-by-twelve array, consistent with standard 96-well microplate geometry. However, in other examples, more or fewer Fresnel lenses 804 may be included according to a defined number of wells and defined geometry of the microplate. Thus, each Fresnel lens 804 may be aligned with one well of the microplate, and each well of the microplate may have a Fresnel lens positioned thereover. The lid substrate 802 may have a complementary geometry to the microplate so that it covers a top portion and sides of the microplate. The plurality of Fresnel lenses 804 may be fused to a flat, top portion of the lid substrate 802. The lid substrate 802 may be formed of acrylic or other polymer (e.g., polystyrene, polycarbonate, etc.), glass, quartz, or any other suitable material for covering the microplate 26. The material of at least the top, flat portion of the lid substrate 802 (e.g., on which the plurality of Fresnel lenses 804 are coupled) may be UV-transparent such that the UV-B/C irradiation passes through the top, flat portion of the lid substrate 802. Furthermore, the material of the lid substrate 802 may be selected in part due to its ability to withstand repeated UV-B/C irradiation. For example, the Fresnel lens microplate cover 800 may be reusable, such that one Fresnel lens microplate cover 800 may be used to cover a plurality of microplates in successive sterilization cycles.

As an example, a user of the microplate irradiation system 10 of FIG. 1 may position the Fresnel lens microplate cover 800 on a first microplate 26 to be irradiated prior to inserting the first microplate 26 into the drawer 25. In such an example, the Fresnel lens microplate cover 800 may serve as the optical components 30 shown in FIG. 1. The user may then initiate a sterilization cycle, such as via the user interface 27 of FIG. 1. After the sterilization cycle is completed, the user may remove the sterilized first microplate 26 from the drawer 25, remove the Fresnel lens microplate cover 800 from the sterilized first microplate, place the Fresnel lens microplate cover 800 atop a second microplate 26 to be irradiated, and repeat the process.

FIG. 9A shows a perspective view 900 of the linear array 19 introduced in FIG. 1 positioned vertically above (e.g., with respect to the z-axis of reference axes 999) the microplate 26 including a plurality of wells 908, such as at a vertical distance 906. Components of FIGS. 9A-9C previously introduced in FIG. 1 are numbered the same and may not be reintroduced. For clarity, optical components are not explicitly illustrated, although it should be understood that optical components may be positioned between the linear array 19 and a top surface of the microplate 26 and aligned with each of the wells 908. For example, the optical components may be included in a cover, such as the microplate cover 800 of FIG. 8. Furthermore, microplate 26 may be inserted inside a cavity (e.g., drawer 25) of the microplate irradiation system 10.

The linear array 19 is shown positioned at a left-most (e.g., smallest y-value with respect to the reference axes 999) position of the microplate 26 in the perspective view 900. In order to sterilize the microplate 26, the linear array 19 may be linearly translated in the y-direction across a width of the microplate 26 in a space above the microplate 26, such as in a scanning direction 904, until reaching a right-most position of the microplate 26. As the linear array 19 is translated in the scanning direction 904, the vertical distance 906 between the microplate 96 and the linear array 19 is maintained such that the linear array 19 does not touch the microplate 26. During the scanning, the plurality of light sources 20 may be activated to emit the radiant output 24, which is directed vertically down to the microplate 26. As shown in FIG. 9A, a width 912 of the microplate 26 is larger than a width 916 of the linear array 19. Furthermore, a length 914 of the linear array 19 (e.g., in the x-direction) may be longer than a length 910 of the microplate 26, at least in some examples. Therefore, the linear array 19 does not span the entire width 912 of the microplate 26, but does span the entire length 910 of the microplate 26.

In the example of FIG. 9A, the linear array 19 is shown with the plurality of light sources 20 arranged in a single line (e.g., aligned in the x-direction with respect to reference axes 999). However, other configurations are also possible, including multiple subarrays within linear array 19 for a two-dimensional linear array. A top view of a first example configuration 925 of the linear array 19 including a plurality of subarrays 919 is shown in FIG. 9B, and a top view of a second example configuration 950 of the linear array 19 including the plurality of subarrays 919 is shown in FIG. 9C.

In both the first example configuration 925 shown in FIG. 9B and the second example configuration 950 shown in FIG. 9C, each of the plurality of subarrays 919 includes the plurality of light sources 20 arranged linearly in the x-direction. The first example configuration 925 of FIG. 9B shows the light sources 20 in the plurality of subarrays 919 arranged at a first example offset (e.g., the light sources 20 of the plurality of subarrays 919 are not aligned with respect to the y-direction), and the second example configuration 950 of FIG. 9C shows the light sources 20 in the plurality of subarrays 919 arranged at a second example offset, although other offsets are also possible. Furthermore, the linear array 19 in both the first example configuration 925 of FIG. 9B and the second example configuration 950 of FIG. 9C may have the same length 914 as the single linear array 19 shown in FIG. 9A. Additionally, the linear array 19 in both the first example configuration 925 of FIG. 9B and the second example configuration 950 of FIG. 9C may have a width 918, which may be wider than the width 916 of the single linear array 19 shown in FIG. 9A and smaller than the width 912 of the microplate 26 shown in FIG. 9A. For example, the width 918 may be wider than the width 916 shown in FIG. 9A to accommodate the plurality of subarrays 919. Although the examples of FIGS. 9B and 9C show three subarrays 919, configurations with more (e.g., greater than three) or fewer (e.g., two) subarrays are also possible.

Figure 10:
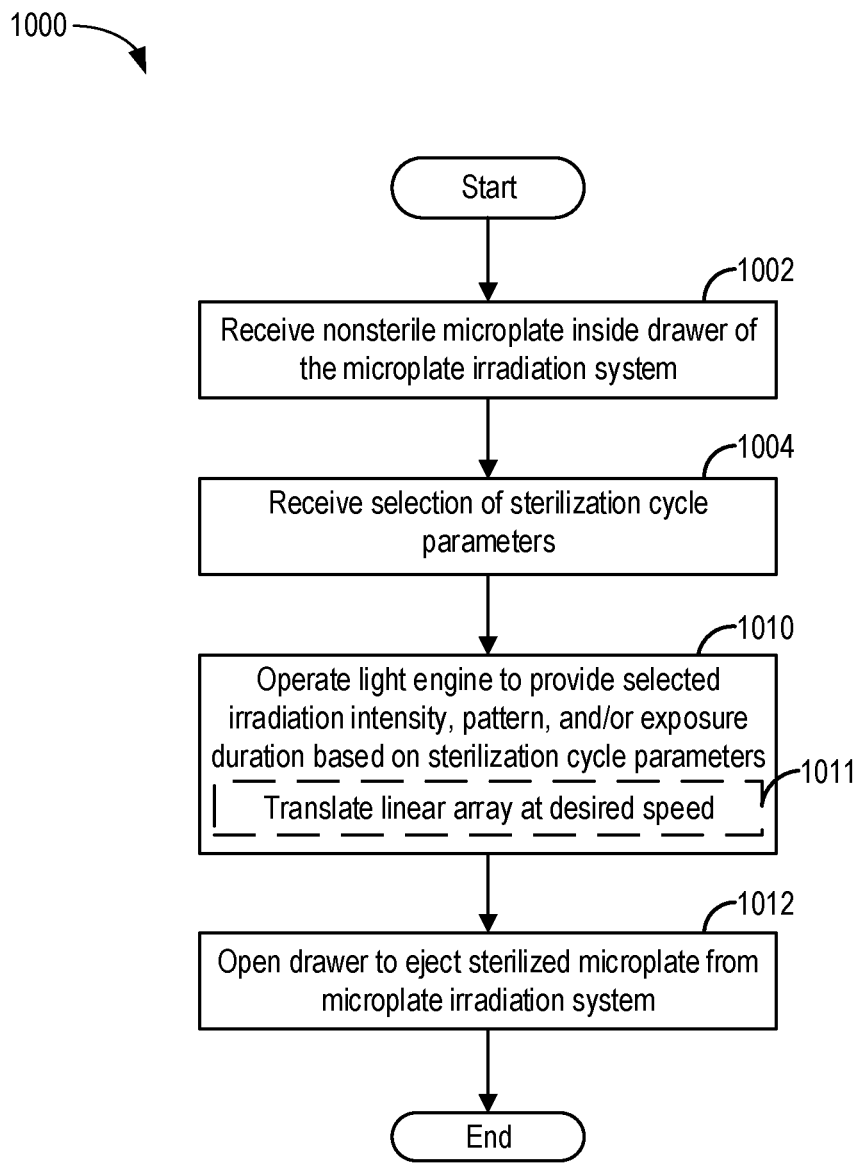
FIG. 10 is an example method for operating the microplate irradiation system.

An example method 1000 for operating a microplate irradiation system is illustrated in a flowchart in FIG. 10. In one example, the method 1000 may be used to operate the microplate irradiation system 10 shown in FIG. 1. Instructions for carrying out the method 1000 may be executed by a controller, for example, the controller 14 of FIG. 1, based on instructions stored on a memory of the controller and in conjunction with signals received by the controller from the user interface 27, the power source 16, the coupling electronics 22, the external device 34, etc.

The method 1000 begins at 1002 and includes receiving a nonsterile microplate inside the drawer of the microplate irradiation system (e.g., drawer 25 of FIG. 1). For example, a user of the microplate irradiation system may position the microplate (e.g., microplate 26 shown in FIG. 1) along an even (e.g., flat) surface of the drawer, with the wells of the microplate facing away from the even surface. After the microplate is positioned inside the drawer, the drawer may be inserted back into a housing of the microplate irradiation system. In another example, the microplate may be positioned directly inside the housing, such as in a cavity, through an opening accessible through a door or flap coupled to the opening. Therefore, closing of the door or flap may cover the cavity. In other examples, the microplate irradiation system may be configured to hold other equipment or reagent-holding devices, such as microscope slides, tissue culture plates, etc., in addition to or alternatively to the microplate. The microplate inside of the housing is positioned below a light engine of the microplate irradiation system (e.g., light engine 12 of FIG. 1) with optical components positioned in between. For example, the optical components (e.g., optical components 30 of FIG. 1) may be immobilized on top of wells of the microplate such that the light engine may direct irradiation to the microplate via the optical components. For example, one or more optical lenses may be positioned on top of each well, as illustrated with respect to FIGS. 2A-2C, 3, and FIGS. 5-7, such as in an array, as illustrated with respect to FIG. 8. Once the microplate is positioned inside of the housing, light from outside of the housing may be prevented from reaching the microplate.

At 1004, the method 1000 includes receiving a selection of sterilization cycle parameters. In one example, the parameters may be selected by the user via the user interface. For example, the user may select the parameters from a menu displayed on a screen of the user interface, and the selected parameters may be relayed to the controller. Thus, at 1004, the method may include the controller receiving the selection of one or more sterilization parameters from a user interface, according to user inputs at the user interface. The selected parameters may include duration of irradiation, pattern of irradiation (e.g., which light sources of the light engine are activated, a scanning speed, etc.), an irradiation intensity, a dose of irradiation, etc. In another example, the irradiation parameters may be selected through the external device, which may be a computer, a USB drive, etc., that may be relayed through a port of the microplate irradiation system or through a wireless network to the controller. In still another example, the controller may select the sterilization parameters according to a predetermined sterilization cycle, which may be selected by the user via the user interface or the external device.

At 1010, method 1000 includes operating the light engine to provide the selected irradiation intensity, pattern, and/or exposure duration based on the sterilization cycle parameters. For example, a plurality of light sources included in a linear array of the light engine (e.g., light sources 20 of linear array 19 of FIG. 1) may be activated at the selected intensity to deliver germicidal UV radiation to the microplate at the selected dose. As an example, the light engine may include a combination of light sources with different emission wavelengths, output wattage, etc., and the activated light sources may be selected to achieve a desired spectral irradiance profile for the selected sterilization cycle. Therefore, the activated light sources and/or the intensity of the light sources may be varied for different selected sterilization cycles. Furthermore, as indicated at 1011, the linear array may be translated across the microplate at a distance above the microplate in an orthogonal direction at a desired speed in order to achieve the selected dose and duration of irradiation. For example, the linear array may be translated at a speed that is pre-calibrated to deliver at least a threshold irradiation intensity and/or dose to a plurality of targeted areas of the microplate, including the sidewall area close to the bottom of the well, for at least a threshold duration, resulting in complete and effective sterilization of each targeted area, and thus, the entire microplate. Specifically, the linearly array may be translated at the determined speed while (e.g., at the same time as) the light sources of the linear array are outputting light at the selected irradiation intensity, pattern, and/or exposure duration. For example, the light sources of the linear array may continuously output light during the entire translation of the linear array across the microplate (e.g., from a first, leftmost position to a final, rightmost position) so that by the end of the translation, the entire top surface area of the microplate has been irradiated.

After the irradiation cycle is complete, at 1012, method 1000 includes opening the drawer to eject the sterilized, irradiated microplate from the housing of the microplate irradiation system. For example, the user may remove the sterilized microplate from the even surface of the drawer after the microplate is ejected. Following 1012, method 1000 ends.

In this way, a high intensity dose of germicidal UV radiation may be delivered to a microplate inside a chamber of a microplate irradiation system via a light engine, including a linear array of light emitting diodes, and optical lenses immobilized on top of wells of the microplate. By linearly translating the linear array in a scanning motion across the microplate, the entire microplate may be irradiated with fewer light emitting diodes compared with a static two-dimensional array that simultaneously irradiates the entire microplate. Furthermore, by including the optical lenses, the UV radiation may be directed to niche areas of each well, including a sidewall and bottom corner of each well, to more effectively sterilize the niche areas compared to when the optical lenses are not included.

The technical effect of using a scanning UV light source to irradiate a microplate and an optical lens aligned with each well of the microplate is that a scanning illumination pattern of high intensity irradiation is achieved across an inner surface of each well, resulting in well sterilization.

The disclosure also provides support for an irradiation system, comprising: a plurality of light sources, each of the plurality of light sources included in a linear array and configured to emit radiation downward, relative to a vertical direction, toward an irradiation surface, the irradiation surface adapted to receive a microplate including a plurality of wells, an actuation system configured to move the emitted radiation linearly in an orthogonal direction, relative to the vertical direction, across the plurality of wells, and one or more optical components positioned between the linear array and the microplate, with respect to the vertical direction, wherein actuation of the linear array directs radiation emitted by the plurality of light sources through a material of the optical components and focuses the radiation, and wherein the focused radiation is directed to a bottom and sidewall regions of the plurality of wells. In a first example of the system, the actuation system is configured to move the emitted radiation across the plurality of wells by moving the linear array in the orthogonal direction relative to the microplate. In a second example of the system, optionally including the first example, the actuation system is configured to move the emitted radiation across the plurality of wells by moving the microplate in the orthogonal direction relative to the microplate.

The disclosure also provides support for an irradiation system, comprising: a plurality of light sources arranged in a two-dimensional array, each of the plurality of light sources configured to emit radiation downward, relative to a vertical direction, toward an irradiation surface, the irradiation surface adapted to receive a microplate including a plurality of wells, an actuation system configured to move the emitted radiation linearly in an orthogonal direction, relative to the vertical direction, across the plurality of wells, and one or more optical components positioned between the linear array and the microplate, with respect to the vertical direction, wherein actuation of the linear array directs radiation emitted by the plurality of light sources through a material of the optical components and focuses the radiation, and wherein the focused radiation is directed to a bottom and sidewall regions of the plurality of wells. In a first example of the system, the plurality of light sources is further arranged in one or more subarrays of the two-dimensional array, each subarray configured as a linear array. In a second example of the system, optionally including the first example, the plurality of light sources of each subarray is offset from the plurality of light sources of one or more adjacent subarrays along the orthogonal direction. In a third example of the system, optionally including one or both of the first and second examples, the plurality of light sources includes a combination of light sources with one or more of different emission wavelengths and different output wattages.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

FIGS. 1-8 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. An irradiation system, comprising:
a plurality of light sources, each of the plurality of light sources included in a linear array and configured to emit radiation downward, relative to a vertical direction, toward an irradiation surface, the irradiation surface including a microplate having a plurality of wells;

an actuation system including an electric motor, the electric motor configured to move the emitted radiation linearly in an orthogonal direction, relative to the vertical direction, across the plurality of wells; and one or more optical components positioned between the linear array and the microplate, with respect to the vertical direction, wherein actuation of the linear array directs radiation emitted by the plurality of light sources through a material of the one or more optical components and focuses the radiation, and wherein the focused radiation is directed to a bottom and sidewall regions of the plurality of wells.

2. The irradiation system of claim 1, wherein the actuation system is configured to move the emitted radiation across the plurality of wells by moving the linear array in the orthogonal direction relative to the microplate.

3. The irradiation system of claim 1, wherein the actuation system is configured to move the emitted radiation across the plurality of wells by moving the microplate in the orthogonal direction relative to the microplate.

4. An irradiation system, comprising:
a plurality of light sources arranged in a two-dimensional array, each of the plurality of light sources configured to emit radiation downward, relative to a vertical direction, toward an irradiation surface, the irradiation surface including a microplate having a plurality of wells;
an actuation system including an electric motor, the electric motor configured to move the emitted radiation linearly in an orthogonal direction, relative to the vertical direction, across the plurality of wells; and
one or more optical components positioned between the two-dimensional array and the microplate, with respect to the vertical direction, wherein actuation of the two-dimensional array directs radiation emitted by the plurality of light sources through a material of the one or more optical components and focuses the radiation, and wherein the focused radiation is directed to a bottom and sidewall regions of the plurality of wells.

5. The irradiation system of claim 4, wherein the plurality of light sources is further arranged in one or more subarrays of the two-dimensional array, each subarray configured as a linear array.

6. The irradiation system of claim 5, wherein the plurality of light sources of each of the one or more subarrays is offset from the plurality of light sources of one or more adjacent subarrays along the orthogonal direction.

7. The irradiation system of claim 4, wherein the plurality of light sources includes a combination of light sources with one or more of different emission wavelengths and different output wattages.

8. An irradiation system, comprising:
an array of light sources, the array of light sources configured to emit radiation downward, relative to a vertical direction, toward an irradiation surface, the irradiation surface including a microplate having a plurality of wells;
an actuation system including an electric motor, the electric motor configured to move the emitted radiation linearly in an orthogonal direction, relative to the vertical direction and relative to the plurality of wells; and
one or more optical components positioned between the array of light sources and the microplate, with respect to the vertical direction, wherein actuation of the emitted radiation directs radiation emitted by the array of light sources through a material of the one or more optical components and focuses the emitted radiation, and wherein the focused emitted radiation is directed to a bottom and sidewall regions of the plurality of wells.

9. The system of claim 8, wherein the electric motor is configured to move the emitted radiation linearly in the orthogonal direction while maintaining a vertical distance between the microplate and the array of light sources.

10. The system of claim 8, wherein a length of the array of light sources, perpendicular to the orthogonal direction and the vertical direction, spans a length of the microplate.

11. The system of claim 10, wherein a width of the array of light sources, perpendicular to the vertical direction and parallel to the orthogonal direction, is less than a width of the microplate.

12. The system of claim 8, wherein the one or more optical components includes a spherical ball lens.

13. The system of claim 12, wherein the spherical ball lens is positioned to be within a top opening of and partially protruding into one of the plurality of wells.

14. The system of claim 8, wherein each of the plurality of wells includes a hollow cylinder open at a top end and closed at a bottom, the hollow cylinder including sidewalls that are perpendicular to the bottom.

15. The system of claim 8, wherein the electric motor is further configured to pause the moving of the emitted radiation in the orthogonal direction, relative to the vertical direction and relative to the plurality of wells.

16. The system of claim 8, wherein the one or more optical components includes a half-ball lens.

17. The system of claim 16, wherein the one or more optical components includes a first half-ball lens and a second half-ball lens positioned over a top opening of one of the plurality of wells, wherein the second half-ball lens partially protrudes into the top opening.

18. The system of claim 17, wherein the first half-ball lens is positioned atop a flat plate and the second half-ball lens is positioned below the flat plate.

19. The system of claim 18, wherein the first half-ball lens and the second half-ball lens are symmetrically aligned and vertically reflected with respect to one another on opposite sides of the flat plate.

20. The system of claim 8, wherein the one or more optical components includes a lens microplate cover, wherein the lens microplate cover includes a plurality of lenses arranged within a substrate, and wherein the lens microplate cover seals and covers the microplate.

* * * * *